United States Patent [19]

Sung et al.

[11] 4,257,780
[45] Mar. 24, 1981

[54] FUEL COMPOSITIONS CONTAINING OXAZOLONIUM HYDROXIDES

[75] Inventors: Rodney L. Sung, Fishkill; Peter Dorn, Lagrangeville, both of N.Y.

[73] Assignee: Texaco Inc., White Plains, N.Y.

[21] Appl. No.: 101,651

[22] Filed: Dec. 10, 1979

[51] Int. Cl.$^3$ .............................................. C10L 1/22
[52] U.S. Cl. ......................................... 44/63; 44/71; 252/392; 548/228
[58] Field of Search ...................... 548/228; 44/41, 63; 252/392

[56] References Cited

U.S. PATENT DOCUMENTS

| | | | |
|---|---|---|---|
| 2,207,063 | 7/1940 | Liston | 44/71 |
| 3,745,168 | 7/1973 | Merritt et al. | 548/228 |
| 3,773,479 | 11/1973 | Dorn et al. | 44/71 |
| 4,038,414 | 7/1977 | Jaeggi et al. | 548/228 |

*Primary Examiner*—Patrick Garvin
*Assistant Examiner*—Y. Harris-Smith
*Attorney, Agent, or Firm*—Carl G. Ries; Robert A. Kulason; Henry W. Archer

[57] ABSTRACT

Described are fuel compositions containing oxazolonium hydroxides as detergent and corrosion inhibitor additives.

8 Claims, No Drawings

FUEL COMPOSITIONS CONTAINING OXAZOLONIUM HYDROXIDES

FIELD OF THE INVENTION

This invention relates to fuels for internal combustion engines and more particularly to the provision of a novel multipurpose additive for such fuels.

As is well known, hydrocarbon fuels have a tendency to form polymeric materials (variously called "gum" or "sludge" or "varnish") in various parts of fuel systems. These resin-like deposits tend to form in the fuel supply lines, fuel filter, carburetor, fuel control injectors, intake manifold and valve stems. Such deposits are objectionable not only because of their effect on mechanical performance but also because they decrease the breathing efficiency in engines of the spark ignition type.

Although each type of fuel is composed essentially of hydrocarbons their stability characteristics differ considerably. Thus typical automotive fuels contain straight and branched chain compounds while aircraft fuels contain a smaller proportion of olefins. Currently, certain types of fuels contain increased amounts of cracked stocks resulting in a higher olefin content and an increased susceptibility to the formation of gum.

The subject fuels generally contain minor amounts of impurities which can promote corrosion during the time when the fuel is transported and stored and even in the fuel tank, fuel lines and carburetors of the engine. Consequently a motor fuel must contain a corrosion inhibitor.

For obvious reasons, it is advantageous to use a multipurpose additive which provides both detergency and corrosion inhibiting properties to the fuel.

DESCRIPTION OF PRIOR DISCLOSURES

Over the years a number of compounds have been suggested as multipurpose additives.

Among disclosures of interest are U.S. Pat. No. 3,909,781 which reports aliphatic hydrocarbon-substituted succinamic acids useful as detergents and corrosion inhibitors; U.S. Pat. No. 3,773,479 which reports substituted asparagines suitable for the same purposes; U.S. Pat. No. 2,207,063 which discloses the use of N(p-hydroxyphenyl) dihydrocarbyl aspartate esters as gum inhibitors for hydrocarbon fuel oil; and U.S. Pat. No. 3,502,451 which discloses motor fuel compositions containing polymers and copolymers of $C_2$ to $C_6$ unsaturated hydrocarbons and the corresponding hydrogenated polymers and copolymers having molecular weights ranging from about 500 to 3,500.

SUMMARY OF THE INVENTION

The invention provides novel oxazolonium hydroxides having utility as fuel additives which are represented by the following structure:

$$\begin{array}{c} R-\overset{+}{N}\underset{\underset{R'-C}{\overset{\|}{}}}{\rule{0pt}{12pt}}-\overset{\|}{C}-\overset{\overset{O}{\|}}{C}-CH_2-\overset{|}{N}-R \\ \phantom{R-N}\diagdown\phantom{xx}\diagup\phantom{xx}\diagdown\phantom{xx} \\ \phantom{xxxxxx}O\phantom{xxx}O^-\phantom{xxx}R' \end{array}$$

Wherein R stands for a hydrocarbyl radical having from 1 to 5 carbon atoms and R' is a hydrocarbyl radical having from 10 to 20 carbon atoms.

Preferred compounds are those where the substituent R group has from 1 to 3 carbon atoms and R' has from 12 to 13 carbon atoms in the chain.

Both the R and R' radicals can be straight chain or branched and may be substituted with one or more typical non-interfering substituents such as halogen, cyano, trifluoromethyl, nitro or alkoxy.

The invention also provides a motor fuel composition comprising a mixture of hydrocarbons in the gasoline boiling range containing a minor, detergent and corrosion inhibiting amount of at least one of the above compounds. Preferably, the amount ranges from 20 to 200 parts per thousand barrels of fuel to provide both detergency and corrosion inhibiting effects. As little as 2.5 parts per 1,000 barrels will provide corrosion inhibition.

DISCLOSURE

The subject substituted oxazolonium hydroxides are prepared by dissolving the corresponding glycine in an inert solvent, preferably, nitromethane and adding the resulting solution to dicyclohexyl carbodiimide. The mixture is heated to around 43° C. and filtered to give the solid compound.

The invention is further illustrated by the following examples.

EXAMPLE I

Preparation of Anhydro-2-Lauroyl-3-Methyl-4-(N,N'Methyl-Lauroyl-Glycyl)-5-Hydroxy-1,3-Oxazolonium Hydroxide.

Forty-five parts of N,N'-methyl Lauroyl glycine were dissolved in 125 parts nitromethane. To the mixture, 35 parts of dicyclohexyl carbodiimide in 125 parts nitromethane was added. The mixture was heated at 43° C. for 2 hours, then filtered. The filtrate was stripped to yield the desired product. The structure was confirmed by IR and NMR.

EXAMPLE II

The procedure of Example I was repeated using N,N'-methyl cocoyl glycine yielding anhydro-2-cocoyl-3-methyl-4-(N,N'-methyl-cocoyl-glycyl)-5-hydroxy-1,3 oxazolonium hydroxides.

Other compounds where R and R' are as above stated are prepared in similar fashion.

Any gasoline suitable for a spark-ignited, internal combustion engine can be used in the practice of this invention. In general, the base fuel will consist of a mixture of hydrocarbons in the gasoline boiling range i.e., boiling from about 75° to 450° F. The hydrocarbon components can consist of paraffinic, naphthenic, aromatic and olefinic hydrocarbons. This gasoline can be obtained naturally or it can be produced by thermal or catalytic cracking and/or reforming of petroleum hydrocarbons. The base fuel will generally have a Research Octane Number above 85 and up to about 102 with the preferred range being from about 90 to 100.

The present additives were tested for effectiveness in the carburetor detergency test. This test is run on a Chevrolet V-8 engine mounted on a test stand using a modified four-barrel carburetor. The two secondary barrels of the carburetor are sealed and the feed to each of the primary barrels arranged so that the detergent additive fuel can run in one barrel and the reference fuel run in the other. The primary carburetor barrels were also modified to contain removable aluminum inserts in the throttle plate area so that the deposits formed on the inserts could be conveniently weighted.

In the procedure designed to determine the effectiveness of an additive fuel to remove preformed deposits in the carburetor, the engine is run for a period of time, usually 24 to 48 hours, using the base fuel as the feed to both barrels with engine blow-by circulated to the air inlet of the carburetor. The weight of the deposits on both sleeves is determined and recorded. The engine is then cycled for 24 additional hours with a reference fuel being fed to one barrel, additive fuel to the other, and no blow-by to the carburetor air inlet. The reference fuel contains 15 PTB of a carburetor detergent. The inserts are then removed from the carburetor and weighed to determine the difference between the performance of the additive and nonadditive fuels in removing the preformed deposits. After the aluminum inserts are cleaned, they are replaced in the carburetor and the process repeated with the fuels reversed in the carburetor to minimize differences in fuel distribution and barrel construction. The effectiveness of the additive fuel is expressed as the difference ($\Delta$) between deposit removed by the additive fuel and the deposit removed by base fuel. When ($\Delta$) is positive, the additive fuel has removed more deposit than the reference fuel.

The motor fuel used as a standard for comparison purposes in this test is a commercial high octane premium gasoline containing a highly effective carburetor detergent. The fuel composition representative of the invention consisted of Base Fuel A described above containing the indicated amounts of the additive of the invention. The results of this test are reported as the difference in carburetor deposits removed by the additive containing gasoline of the invention in comparison to the commercial premium detergent gasoline.

The results of the Chevrolet Carburetor Detergency Test are set forth in Table I below.

The base fuel employed in the following examples was a premium grade gasoline having a Research Octane Number of about 100 and containing 3 cc. of tetraethyl lead per gallon. This gasoline consisted of about 25 percent aromatic hydrocarbons, 10 percent olefinic hydrocarbons and 65 percent paraffinic hydrocarbons and boiled in the range from about 90° F. to 380° F.

TABLE I

CARBURETOR DETERGENCY TEST

| Run | Additive in S.C. + 3g./gal. Pb | % Deposit Removal Additive Fuel | % Deposit Removal Reference Fuel[1] | Percent Change |
|---|---|---|---|---|
| 1 | 0.2 (V)% Commercial multipurpose fuel additive[a] | 41 | +10[b] | +51 vs. A |
| 2 | 100 PTB[2] Anhydro-2-Lauroyl-3-methyl-4-(N,N'-Methyl Lauroyl Glycyl)-5 Hydroxy 1,3-oxazolonium hydroxide | 76 | 81 | −5 vs. B |
| 3 | 75 PTB[2] Anhydro-2-Cocoyl-3-methyl-4-(N,N'-Methyl Cocoyl glycyl) 5-hydroxy-1,3-oxazolonium hydroxide | 67 | 85 | −18 vs. B |
| 4 | 0.218 (V)% multipurpose fuel additive[c] | 45 | 88 | −43 vs. B |
| 5 | 0.20 (V)% multipurpose fuel additive[a] | 41 | 40 | +1 vs. C |

[1]Reference Fuel A = Base Fuel, B = 1035 PTB of a commercial detergent package containing: N-butyl alcohol 15%; aromatic distillates 34%, polyisobutylenes 4%; polyisobutylenamines 9%; mineral oil 38%, C = 0.218(V)% of [c].
[a]Contains 15 PTB of the reaction product of maleic anhydride and Armeen L15 in mineral oil.
[b]"+" denotes fuel deposit build-up.
[c]Contains 50 PTB of a commercial additive package containing; aromatic distillates 28%; isooctyl alcohols 21%; polybutanes 5%; N-polyamine-alkenyl succinimides 44%.
[2]PTB - additive concentration in pounds per thousand barrels of gasoline.

Table I shows that on a weight-to-weight basis the present compounds are more effective than commercial additives.

The additives of the invention also have anti-corrosion properties as shown by their performance in the National Association of Corrosion Engineers (NACE) Rusting Test. In this test a determination is made of the ability of motor gasolines to inhibit the rusting of ferrous parts when water becomes mixed with gasoline. Briefly stated, the test is carried out by stirring a mixture 300 ml of the test gasoline and 30 ml of water at 37.8° C. with a polished steel specimen completely immersed therein for a test period of 3½ hours. The percentage of the specimen that has rusted is determined by comparison with photographic standards. Further details of the procedure appear in NACE Standard TM-01-72 and ASTM D6651 1P-135 (Procedure A).

Table II below shows the results of this test for a representative compound of the invention at different concentrations in pounds per 1,000 barrels (PTB) in and against an unleaded base fuel (UBF).

The data of Table show that as little as 2.5 PTB of the additive substantially eliminates rusting.

The fuels of the invention may contain any additive conventionally employed in gasoline. Tetraalkyl lead, antiknock additives, dyes, corrosion inhibitors, anti-oxidants and the like can be beneficially employed without materially affecting the additive of the invention.

TABLE II

| Concentration | Additive | Rate % Rust |
|---|---|---|
| 7.5 PTB Check | Anhydro-2-Lauroyl-3-4-(N,N' Methyl lauroyl glycyl)-5 hydroxy-1,3-oxazolonium hydroxide plus unleaded base fuel | 1-5 |
| 7.5 PTB | Anhydro-2-Lauroyl-3-4-(N,N' Methyl lauroyl glycyl)-5 hydroxy-1,3-oxazolonium hydroxide + U.B.F. | Trace |
| 5 PTB | Anhydro-2-Lauroyl-3-4-(N,N' Methyl lauroyl glycyl)-5 hydroxy-1,3-oxazolonium hydroxide + U.B.F. | Trace |
| 5 PTB | Anhydro-2-Lauroyl-3-4-(N,N' Methyl lauroyl glycyl)-5 hydroxy-1,3-oxazolonium hydroxide + U.B.F. | Trace |
| 2.5 PTB | Anhydro-2-Lauroyl-3-4-(N,N' Methyl lauroyl glycyl) | Trace |

TABLE II-continued

| Concentration | Additive | Rate % Rust |
|---|---|---|
| 2.5 PTB | -5 hydroxy-1,3-oxazolonium hydroxide + U.B.F. Anhydro-2-Lauroyl-3-4-(N,N' Methyl lauroyl glycyl) -5 hydroxy-1,3-oxazolonium hydroxide + U.B.F. | Trace |
| Unleaded Base Fuel (UBF) | Anhydro-2-Lauroyl-3-4-(N,N' Methyl lauroyl glycyl) -5 hydroxy-1,3-oxazolonium hydroxide + U.B.F. | 50–100 |
| Check | Anhydro-2-Lauroyl-3-4-(N,N' Methyl lauroyl glycyl) -5 hydroxy-1,3-oxazolonium hydroxide + U.B.F. | |
| Unleaded Base Fuel (UBF) | Anhydro-2-Lauroyl-3-4-(N,N' Methyl lauroyl glycyl) -5 hydroxy-1,3-oxazolonium hydroxide + U.B.F. | 50–100 |

What is claimed is:

1. An oxazolonium hydroxide of the formula:

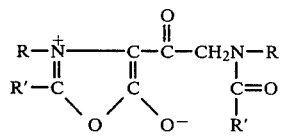

wherein R is a hydrocarbyl radical having from 1 to 5 carbon atoms and R' is a hydrocarbyl radical having from 10 to 20 carbon atoms.

2. The compound of claim 1, being anhydro-2-lauroyl-3-methyl-4-(N'N'-methyl lauroyl-glycyl)-5-hydroxy-1,3-oxazolonium hydroxide.

3. The compound of claim 1, being anhydro-2-cocoyl-3-methyl-4-(N,N'-methyl-cocoyl-glycyl)-5-hydroxy-1,3-oxazolonium hydroxide.

4. A motor fuel composition comprising a mixture of hydrocarbons in the gasoline boiling range containing a detergent and corrosion inhibiting amount of a compound of claim 1.

5. The composition of claim 4, wherein said compound is anhydro-2-lauroyl-3-methyl-4-(N,N'-methyl-lauroyl-glycyl)-5-hydroxy-1,3-oxazolonium hydroxide.

6. The composition of claim 4, wherein said compound is anhydro-2-lauroyl-3-methyl-4-(N,N'-methyl lauroyl-glycyl)-5-hydroxy-1,3-oxazolonium hydroxide.

7. The composition of claim 4, containing at least 2.5 parts of said additive per thousand barrels.

8. The composition of claim 4, containing from about 20 to 200 parts of said additive per thousand barrels.

* * * * *